(12) United States Patent
Yamasaki

(10) Patent No.: US 9,248,102 B2
(45) Date of Patent: Feb. 2, 2016

(54) TABLET CONTAINING 5-HYDROXY-1H-IMIDAZOLE-4-CARBOXAMIDE

(71) Applicant: FUJIFILM Corporation, Tokyo (JP)

(72) Inventor: Yasuomi Yamasaki, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/528,768

(22) Filed: Oct. 30, 2014

(65) Prior Publication Data

US 2015/0057324 A1 Feb. 26, 2015

Related U.S. Application Data

(63) Continuation of application No. PCT/JP2014/050591, filed on Jan. 15, 2014.

(30) Foreign Application Priority Data

Jan. 15, 2013 (JP) .................................. 2013-004995

(51) Int. Cl.
*A61K 9/20* (2006.01)
*A61K 31/4164* (2006.01)

(52) U.S. Cl.
CPC .............. *A61K 9/2095* (2013.01); *A61K 9/2009* (2013.01); *A61K 31/4164* (2013.01); *A61K 9/20* (2013.01); *A61K 9/2054* (2013.01)

(58) Field of Classification Search
CPC ...... A61K 9/20; A61K 9/2054; A61K 9/2095
USPC ....................................................... 424/464
See application file for complete search history.

(56) References Cited

U.S. PATENT DOCUMENTS

| 4,181,731 | A | 1/1980 | Yoshida et al. |
| 8,664,405 | B2 | 3/2014 | Kato et al. |
| 2010/0210855 | A1 | 8/2010 | Nobuo et al. |

FOREIGN PATENT DOCUMENTS

| EP | 0 159 777 A1 | 10/1985 |
| EP | 2 407 166 A1 | 1/2012 |
| JP | 53-32124 | 3/1978 |
| JP | 58-24569 A | 2/1983 |
| JP | 1-37376 B2 | 8/1989 |
| JP | 9-208468 A | 8/1997 |
| JP | 2007-186470 A | 7/2007 |
| WO | WO 2009/035168 A1 | 3/2009 |

OTHER PUBLICATIONS

PubChem, Open Chemistry Database, Silicon Dioxide and its Synonyms (2008).*
International Search Report, mailed Apr. 22, 2014, issued in PCT/JP2014/050591.
M. C. Gohel, "A review of co-processed directly compressible excipients", J. Pharm. Pharmaceut. Sci., vol. 8, pp. 76-93, 2005.
Oshima et al., "Effect of Size and Shape of Tablets and Capsules on Ease of Grasping and Swallowing (1) : Comparison between Elderly and Students", Jpn. J. Pharm. Health Care Sci., vol. 32, No. 8 (2006), pp. 842-848.
Strategy and new technology for preparation of pharmaceutical formulations (Iyakuhin Seizaika Horyaku to Shin-gijutsu), Chapter 2, p. 47, 2007, CMC Publishing.
Written Opinion of the International Searching Authority, mailed Apr. 22, 2014, issued in PCT/JP2014/050591.
International Search Report on Patentability and Written Opinion of the Internatioanl Searching Authority issued in International Patent Application No. PCT/JP2014/050591 on Jul. 30, 2015.

* cited by examiner

*Primary Examiner* — Kevin E Weddington
(74) *Attorney, Agent, or Firm* — Birch, Stewart, Kolasch & Birch, LLP

(57) ABSTRACT

The tablet containing (1) 5-hydroxy-1H-imidazole-4-carboxamide or a salt thereof, or a hydrate thereof, and (2) silicon dioxide has a high content of 5-hydroxy -1H-imidazole-4-carboxamide or a salt thereof, or a hydrate thereof and an easily takable size as a tablet, and shows superior dissolution property.

11 Claims, No Drawings

TABLET CONTAINING 5-HYDROXY-1H-IMIDAZOLE-4-CARBOXAMIDE

CROSS REFERENCE OF THE RELATED APPLICATION

This application is a Continuation of PCT International Application No. PCT/JP2014/050591, filed on Jan. 15, 2014, which claims priority under 35 U.S.C. 119(a) to Patent Application No. 2013-004995, filed in Japan on Jan. 15, 2013, all of which are hereby expressly incorporated by reference into the present application.

TECHNICAL FIELD

The present invention relates to a tablet containing (1) 5-hydroxy-1H-imidazole-4-carboxamide or a salt thereof, or a hydrate thereof, and (2) silicon dioxide.

BACKGROUND ART

Since 5-hydroxy-1H-imidazole-4-carboxamide (henceforth also referred to as Compound A) or a salt thereof, or a hydrate thereof has a potent carcinostatic action, it is a medically useful compound as an anticancer agent (Patent document 1). In particular, it is an anticancer agent that exhibits a potent efficacy against solid carcinomas, against which chemotherapy has conventionally been considered difficult, and is also a highly safe anticancer agent that shows less side reactions, and thus it is a compound of which clinical applications are expected in a wide range of dosage forms such as oral agent, injection, ointment, and suppository. Tablets containing Compound A or a salt thereof, or a hydrate thereof are orally administered in a number of one to several tablets at one time.

It has been reported that the size of easily takable circular tablets is 7 to 8 mm in diameter, and the size of easily takable elliptical tablets is 9 mm in major axis (Non-patent document 1).

In general, tablets that can be easily handled and are suitable for taking should have appropriate hardness. In order to produce tablets having a required hardness by the direct tableting method, content of additives in tablets should be 60% or more, preferably 70% or more, of the mass of tablets (Non-patent document 2).

There is known a method for increasing base content in tablets by utilizing a binder and the wet granulation method (Non-patent document 3). Further, hardness of tablets can also be increased by using granules for making tablets granulated by a wet or dry granulation method to increase binding power of the granules at the time of tablet making.

Any tablet having a high content of Compound A or a salt thereof, or a hydrate thereof, an easily takable size, and superior dissolution property has not been known so far.

PRIOR ART REFERENCES

Patent Document

Patent document 1: Japanese Patent Unexamined Publication (Kokai) No. 53-32124

Non-Patent Documents

Non-patent document 1: Jpn. J. Pharm. Health Care Sci. (Iryo Yakugaku), vol. 32, pp. 842-848, 2006

Non-patent document 2: J. Pharm. Pharmaceut. Sci., vol. 8, pp. 76-93, 2005

Non-patent document 3: Strategy and new technology for preparation of pharmaceutical formulations (Iyakuhin Seizaika Horyaku to Shin-gijutsu), Chapter 2, p. 47, 2007, CMC Publishing

SUMMARY OF THE INVENTION

Object to be Achieved by the Invention

In order to produce tablets having a required hardness by the direct tableting method, content of additives is required to be higher than a certain level, and a higher content of an active ingredient results in a larger size of tablets. However, tablets having a size of 9 mm or larger are difficult to be taken of course by children and patients suffering from difficulty in swallowing, and even by usual adult patients, because such large tablets give feelings of resistance and pressure, and thus degrade medication compliance. The method of increasing binding power of particles at the time of tablet making to increase hardness of tablets provides required hardness, but increase of the binding power of particles degrades the dissolution property.

For improvement in medication compliance, there are desired tablets that reduce number of tablets to be taken, and are easily taken. That is, it is desired to develop a tablet having a high content of Compound A or a salt thereof, or a hydrate thereof, and an easily takable size.

Means for Achieving the Object

Under such circumstances as mentioned above, the inventor of the present invention conducted various researches. As a result, the inventor of the present invention found that a tablet containing (1) 5-hydroxy-1H-imidazole-4-carboxamide or a salt thereof, or a hydrate thereof, and (2) silicon dioxide could achieve the aforementioned object, and accomplished the present invention.

The present invention provides the followings.

[1] A tablet containing (1) 5-hydroxy-1H-imidazole-4-carboxamide or a salt thereof, or a hydrate thereof, and (2) silicon dioxide.

[2] The tablet according to [1], which further contains an additive.

[3] The tablet according to [2], wherein the additive consists of an additive containing a disintegrating agent.

[4] The tablet according to any one of [1] to [3], wherein silicon dioxide consists of one or more selected from silica gel, silicic anhydride, colloidal silicon dioxide, light anhydrous silicic acid, and hydrated silicon dioxide.

[5] The tablet according to any one of [1] to [3], wherein silicon dioxide consists of one or more selected from light anhydrous silicic acid and hydrated silicon dioxide.

[6] The tablet according to any one of [1] to [5], wherein content of silicon dioxide is 0.1 to 20% of the mass of the tablet.

[7] The tablet according to [3], wherein the disintegrating agent consists of one or more selected from a cellulose derivative, a starch derivative, and a polyvinylpyrrolidone derivative.

[8] The tablet according to [3], wherein the disintegrating agent consists of one or more selected from carmellose calcium, carmellose, low-substituted hydroxypropylcellulose, croscarmellose sodium, carboxymethyl starch sodium, partially pregelatinized starch, and crospovidone.

[9] The tablet according to [3], wherein the disintegrating agent consists of one or more selected from carmellose calcium, low-substituted hydroxypropylcellulose, and partially pregelatinized starch.

[10] The tablet according to [3], wherein the disintegrating agent is carmellose calcium.

[11] The tablet according to any one of [1] to [10], wherein content of 5-hydroxy-1H-imidazole-4-carboxamide or a salt thereof, or a hydrate thereof is 0.3 to 95% of the mass of the tablet.

[12] A method for producing the tablet according to any one of [1] to [11], wherein the tablet is made by using granulated powder produced by a wet granulation method.

[13] The production method according to [12], wherein the wet granulation method is the fluidized bed granulation method.

[14] A tablet obtained by tableting granulated particles containing (1) 5-hydroxy-1H-imidazole-4-carboxamide or a salt thereof, or a hydrate thereof, and (2) silicon dioxide.

[15] The tablet according to [14], which is obtained by tableting granulated powder further containing an additive.

[16] The tablet according to [14], wherein the additive is an additive containing a disintegrating agent.

[17] The tablet according to any one of [14] to [16], wherein silicon dioxide consists of one or more selected from silica gel, silicic anhydride, colloidal silicon dioxide, light anhydrous silicic acid, and hydrated silicon dioxide.

[18] The tablet according to any one of [14] to [16], wherein silicon dioxide consists of one or more selected from light anhydrous silicic acid and hydrated silicon dioxide.

[19] The tablet according to any one of [14] to [18], wherein content of silicon dioxide is 0.1 to 20% of the mass of the tablet.

[20] The tablet according to [16], wherein the disintegrating agent consists of one or more selected from a cellulose derivative, a starch derivative, and a polyvinylpyrrolidone derivative.

[21] The tablet according to [16], wherein the disintegrating agent consists of one or more selected from carmellose calcium, carmellose, low-substituted hydroxypropylcellulose, croscarmellose sodium, carboxymethyl starch sodium, partially pregelatinized starch, and crospovidone.

[22] The tablet according to [16], wherein the disintegrating agent consists of one or more selected from carmellose calcium, low-substituted hydroxypropylcellulose, and partially pregelatinized starch.

[23] The tablet according to [16], wherein the disintegrating agent is carmellose calcium.

[24] The tablet according to any one of [14] to [23], wherein content of 5-hydroxy-1H-imidazole-4-carboxamide or a salt thereof, or a hydrate thereof is 0.3 to 95% of the mass of the tablet.

Effect of the Invention

The tablet of the present invention has a high content of Compound A or a salt thereof, or a hydrate thereof, and an easily takable size as a tablet, and shows superior dissolution property.

MODES FOR CARRYING OUT THE INVENTION

Hereafter, the present invention will be explained in detail.

The symbol "%" used for the present invention means percentage by mass, unless especially indicated. The numerical value ranges shown with "to" in the present invention means ranges including the numerical values indicated before and after "to" as the minimum and maximum values, respectively. In the present invention, when two or more kinds of substances corresponding to one component of a composition are present in the composition, the amount of the component means the total amount of two or more kinds of the substances present in the composition, unless especially indicated.

When the expression "Compound A or a salt thereof, or a hydrate thereof" is used in this invention concerning Compound A (also concerning the indication of "5-hydroxy-1H-imidazole-4-carboxamide"), it is intended to indicate any selected from the group consisting of Compound A, a salt of Compound A, a hydrate of Compound A, and a hydrate of a salt of Compound A, unless especially indicated, and the expression "containing Compound A or a salt thereof, or a hydrate thereof" means to contain at least one selected from the group consisting of Compound A, a salt of Compound A, a hydrate of Compound A, and a hydrate of a salt of Compound A, unless especially indicated.

Compound A or a salt thereof, or a hydrate thereof used for the present invention can be produced by, for example, the method described in Preparation Example 1 mentioned later.

Content of Compound A or a salt thereof, or a hydrate thereof can be 0.3 to 95%, preferably 20 to 90%, more preferably 40 to 85%, of the mass of the tablet.

Silicon dioxide used in the present invention can be mixed in the granulated particles, or out of the granulated particles.

Content of silicon dioxide can be 0.1 to 20%, preferably 0.5 to 15%, more preferably 1 to 5%, of the mass of the tablet.

The content of silicon dioxide is preferably 0.3 to 3% of the mass of the tablet.

The term "mass of tablet" used in this invention for a film-coated tablet means mass of the tablet before coating, unless especially indicated.

Silicon dioxide is not particularly limited, and examples include, for example, silica gel, silicic anhydride, colloidal silicon dioxide, light anhydrous silicic acid, and hydrated silicon dioxide. Light anhydrous silicic acid and hydrated silicon dioxide are preferred.

The additive is not particularly limited, and examples include, for example, disintegrating agent, binder, lubricant, excipient, corrigent, colorant, flavoring agent, acid, surfactant, and plasticizer. Disintegrating agent, binder, lubricant, and excipient are preferred. One or more of these additives may be used in combination, unless especially indicated, and amounts thereof to be mixed are not particularly limited, and can be appropriately determined depending on each purpose so that the effect thereof is sufficiently exhibited.

The disintegrating agent is not particularly limited, and examples include, for example, cellulose derivatives such as carmellose calcium, carmellose, low-substituted hydroxypropylcellulose, and croscarmellose sodium; starch derivatives such as carboxymethyl starch sodium and partially pregelatinized starch; and polyvinylpyrrolidone derivatives such as crospovidone. Carmellose calcium, low-substituted hydroxypropylcellulose, partially pregelatinized starch, and carmellose are preferred, and carmellose calcium is more preferred.

The disintegrating agent can be blended in the granulated particles, or out of the granulated particles.

Content of the disintegrating agent can be 1 to 20%, preferably 3 to 15%, more preferably 5 to 10%, of the mass of the tablet.

The binder is not particularly limited, and examples include, for example, hydroxypropylcellulose, polyvinyl alcohol, povidone, hypromellose, carmellose sodium, methylcellulose, gum arabic, and dextrin. Hydroxypropylcellulose and polyvinyl alcohol are preferred.

Content of the binder can be 1 to 20%, preferably 2.5 to 10%, of the mass of the tablet.

The lubricant is not particularly limited, and examples include, for example, magnesium stearate, calcium stearate, stearic acid, sodium stearyl fumarate, talc, and sucrose fatty acid esters. Magnesium stearate and sodium stearyl fumarate are preferred, and magnesium stearate is more preferred.

Content of the lubricant can be 0.1 to 5%, preferably 0.2 to 5%, more preferably 0.5 to 3%, of the mass of the tablet.

The excipient is not particularly limited, and examples include, for example, sugar alcohols such as erythritol, mannitol, xylitol and sorbitol; saccharides such sucrose, powdered sugar, lactose, and glucose; cyclodextrins such as α-cyclodextrin, β-cyclodextrin, γ-cyclodextrin, hydroxypropyl-β-cyclodextrin, and sulfobutyl ether-β-cyclodextrin sodium; celluloses such as crystalline cellulose and microcrystalline cellulose; and starches such as cornstarch, potato starch and partially pregelatinized starch. Mannitol, lactose, cornstarch, and partially pregelatinized starch are preferred, and lactose and cornstarch are more preferred.

The corrigent is not particularly limited, and examples include, for example, aspartame, saccharin, stevia, thaumatin, and acesulfame potassium.

The colorant it is not particularly limited, and examples include, for example, titanium dioxide, iron sesquioxide, yellow iron sesquioxide, black oxide of iron, Food Red No. 102, Food Yellow No. 4, and Food Yellow No. 5.

The flavoring agent is not particularly limited, and examples include, for example, volatile oils such as orange oil, lemon oil, peppermint oil, and pineapple oil; essences such as orange essence and peppermint essence; flavors such as cherry flavor, vanilla bean flavor and fruit flavor; powder perfumes such as Apple Micron, Banana Micron, Peach Micron, Strawberry Micron, and Orange Micron; vanillin; and ethyl vanillin.

The acid is not particularly limited, and examples include, for example, hydroxycarboxylic acids, and citric acid, tartaric acid, and malic acid are preferred.

The surfactant is not particularly limited, and examples include, for example, sodium lauryl sulfate, dioctyl sodium sulfosuccinate, polysorbates, and polyoxyethylene hydrogenated castor oil.

The plasticizer is not particularly limited, and examples include, for example, triethyl citrate, Macrogol, triacetine, and propylene glycol.

Surface of the tablet of the present invention may be film-coated with a coating agent, if needed.

The coating agent is not particularly limited, and examples include, for example, hypromellose, aminoalkyl methacrylate copolymer E, aminoalkyl methacrylate copolymer RS, ethylcellulose, cellulose acetate phthalate, hypromellose phthalic acid ester, methacrylic acid copolymer L, methacrylic acid copolymer LD, methacrylic acid copolymer S, polyvinyl alcohol, hydroxypropyl methylcellulose acetate succinate, polyvinyl alcohol/acrylic acid/methyl methacrylate copolymer, and polyvinyl alcohol polyethylene glycol graft copolymer. Hypromellose and polyvinyl alcohol are preferred, and hypromellose is more preferred.

Example of salt of Compound A concerning the present invention include commonly known salts at a basic group or acidic group.

Examples of salts of a basic group include, for example, salts with mineral acids such as hydrochloric acid, hydrogen bromide, phosphoric acid, and sulfuric acid; salts with organic carboxylic acids such as tartaric acid, formic acid, acetic acid, fumaric acid, maleic acid, citric acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of salts of an acidic group include, for example, salts with alkali metals such as sodium and potassium; salts with alkaline earth metals such as calcium and magnesium: ammonium salts; and salts with nitrogen-containing organic bases such as trimethylamine, triethylamine, tributylamine, trometamol, pyridine, N,N-dimethylaniline, N-methylpiperidine, N-methylmorpholine, diethylamine, dicyclohexylamine, procaine, dibenzylamine, N-benzyl-β-phenethylamine, and N,N'-dibenzylethylenediamine.

Among the aforementioned salts, preferred salts of Compound A are pharmacologically acceptable salts.

Examples of hydrate of Compound A or a salt thereof concerning the present invention include a hydrate of Compound A produced by the method described in Japanese Patent Unexamined Publication (Kokai) No. 58-24569, a hydrate of Compound A produced by the method described in International Patent Publication WO2009/035168, a hydrate of Compound A produced by the method described in Preparation Example 1 mentioned later, and so forth, and the hydrate of Compound A produced by the method described in Preparation Example 1 is preferred.

When the tablet of the present invention is administered, administration method, dose, and frequency of administration can be appropriately chosen according to age, weight, and symptoms of patients. It can usually be administered in such an amount that the efficacy can be exhibited, and such an amount can be administered one time per day or several times per day as divided portions. It can be usually administered to an adult in an amount of 10 to 5000 mg, preferably 200 to 2500 mg, per day in terms of the amount of Compound A, at one time per day or several times per day as divided portions.

Examples of the method for producing the tablet of the present invention include a method of producing granulated powder by a dry or wet granulation method, adding one or more of an excipient, a disintegrating agent, a lubricant, and so forth as required to prepare mixed powder for tablet making, and making tablets with the powder for tablet making.

As the method for producing granulated powder, a wet granulation method is preferred.

The wet granulation method is not particularly limited, and examples include, for example, fluidized bed granulation method, centrifugal rolling granulation method, agitation granulation method, high-speed agitation granulation method, rolling granulation method, wet pulverization granulation method, and extrusion granulation method. The fluidized bed granulation method, centrifugal rolling granulation method, agitation granulation method, high-speed agitation granulation method, rolling granulation method, and wet pulverization granulation method are preferred, and the fluidized bed granulation method is particularly preferred.

Examples of the method for adding the binder at the time of granulation include (1) a method of spraying a binder dissolved in water on mixed powder containing Compound A or a salt thereof, or a hydrate thereof, (2) a method of adding a binder to mixed powder containing Compound A or a salt thereof, or a hydrate thereof, and spraying water on the mixture, and so forth.

Examples of the method for adding silicon dioxide include (1) a method of adding silicon dioxide in the form of powder to mixed powder containing Compound A or a salt thereof, or a hydrate thereof, (2) a method of adding silicon dioxide in the form of powder to granulation product containing Compound A or a salt thereof, or a hydrate thereof, (3) a method of dispersing silicon dioxide and a binder in water, and spraying the dispersion on mixed powder containing Compound A or a salt thereof, or a hydrate thereof, and so forth, and the method of (3) is preferred.

The tablet of the present invention is preferably a circular tablet. The circular tablet may have sizes of a diameter of 5 to 9 mm and a thickness of 2 to 5 mm, preferably a diameter of 7 to 9 mm and a thickness of 3 to 5 mm.

The tablet of the present invention preferably shows a dissolution ratio of Compound A of 80% or higher, more preferably 85% or higher, after stirring for 15 minutes at a revolution number of 50 rpm in a test solution consisting of the second dissolution test solution according to the Japanese Pharmacopoeia, as determined by the dissolution test method described in the 16th Japanese Pharmacopoeia (paddle method).

When the tablet of the present invention is a circular tablet having a diameter of 8.5 mm, hardness thereof is preferably 30 to 150 N, more preferably 50 to 130 N.

Hereafter, usefulness of the tablet of the present invention will be explained with reference to the following test examples.

For the measurement of hardness of tablets, a tablet hardness meter 8M (Dr. Schleuniger Pharmatron), or a portable checker PC30 (Okada Seiko) was used.

The dissolution test was performed according to the paddle method dissolution test of the Japanese Pharmacopoeia. The revolution number of the paddle was 50 rpm. A sample was put into 900 mL of the second dissolution test solution of the Japanese Pharmacopoeia, the test solution was stirred for 15 minutes and collected, and the dissolution ratio of Compound A (%) was obtained by the extinction method.

TEST EXAMPLE 1

As samples, tablets of Examples 1 to 3 and Comparative Example 1 were used.

The results of the measurement of tablet hardness and dissolution test are shown in Table 1.

TABLE 1

|  | Example 1 | Example 2 | Example 3 | Comparative Example 1 |
| --- | --- | --- | --- | --- |
| Hydrate of Compound A (mg) | 242.1 | 200.0 | 200.0 | 200.0 |
| Lactose hydrate (mg) | — | 10.0 | 7.5 | 12.5 |
| Cornstarch (mg) | — | 13.0 | 10.5 | 15.5 |
| Carmellose calcium (mg) | 26.9 | 10.0 | 10.0 | 10.0 |
| Polyvinyl alcohol (mg) | — | 10.0 | 10.0 | 10.0 |
| Hydroxypropylcellulose (mg) | 11.8 | — | — | — |
| Light anhydrous silicic acid (mg) | 5.9 | 5.0 | 5.0 | — |
| Anhydrous citric acid (mg) | 11.8 | — | 5.0 | — |
| Magnesium stearate (mg) | 1.5 | 2.0 | 2.0 | 2.0 |
| Total (mg) | 300.0 | 250.0 | 250.0 | 250.0 |
| Dissolution ratio of Compound A (%) | 100.6 | 103.9 | 106.0 | 79.1 |
| Hardness (N) | 66 | 73 | 75 | 78 |

The tablets containing light anhydrous silicic acid (Examples 1 to 3) showed notably superior dissolution property compared with the tablet produced by the conventional technique (Japanese Patent Publication (Kokoku) No. 1-37376, Comparative Example 1). Further, the tablets of Examples 1 to 3 had sufficient hardness.

TEST EXAMPLE 2

As samples, the tablets of Examples 4 to 6 and Comparative Example 2 were used.

Measurement of tablet hardness and dissolution test were performed in the same manner as that of Test Example 1. The results are shown in Table 2.

TABLE 2

|  | Example 4 | Example 5 | Example 6 | Comparative Example 2 |
| --- | --- | --- | --- | --- |
| Hydrate of Compound A (mg) | 221.3 | 221.5 | 221.3 | 221.3 |
| Lactose hydrate (mg) | 8.8 | 14.1 | 15.9 | 16.6 |
| Carmellose calcium (mg) | 13.0 | 13.0 | 13.0 | 13.0 |
| Hydroxypropylcellulose (mg) | 7.8 | 7.8 | 7.8 | 7.8 |
| Light anhydrous silicic acid (mg) | 7.8 | 2.3 | 0.8 | — |
| Magnesium stearate (mg) | 1.3 | 1.3 | 1.3 | 1.3 |
| Total (mg) | 260.0 | 260.0 | 260.0 | 260.0 |
| Light anhydrous silicic acid content (%) | 3 | 0.9 | 0.3 | 0 |
| Dissolution ratio of Compound A (%) | 98.9 | 88.8 | 81.3 | 74.5 |
| Hardness (N) | 104 | 107 | 121 | 97 |

The tablets containing 3 to 0.3% of light anhydrous silicic acid (Examples 4 to 6) showed superior dissolution property compared with the tablet not containing light anhydrous silicic acid (Comparative Example 2). In particular, the tablet containing 3% of light anhydrous silicic acid (Example 4) showed extremely superior dissolution property. Further, the tablets of Examples 4 to 6 had sufficient hardness.

TEST EXAMPLE 3

As samples, a tablet containing light anhydrous silicic acid added after granulation (Example 7) and a tablet containing light anhydrous silicic acid added before granulation (Example 8) were used.

Measurement of tablet hardness and dissolution test were performed in the same manner as that of Test Example 1. The results are shown in Table 3.

TABLE 3

|  | Example 7 | Example 8 |
| --- | --- | --- |
| Hydrate of Compound A (mg) | 221.3 | 221.3 |
| Lactose hydrate (mg) | 8.8 | 8.8 |
| Carmellose calcium (mg) | 13.0 | 13.0 |
| Hydroxypropylcellulose (mg) | 7.8 | 7.8 |
| Light anhydrous silicic acid (mg) | 7.8 | 7.8 |
| Magnesium stearate (mg) | 1.3 | 1.3 |
| Total (mg) | 260.0 | 260.0 |
| Dissolution ratio of Compound A (%) | 90.8 | 86.7 |
| Hardness (N) | 52 | 67 |

The tablet containing light anhydrous silicic acid added after granulation (Example 7) and the tablet containing light anhydrous silicic acid added before granulation (Example 8) showed superior dissolution property. Further, the tablets of Examples 7 and 8 had sufficient hardness.

TEST EXAMPLE 4

As samples, the uncoated tablets and film-coated tablets of Examples 9 and 10 were used.

Measurement of tablet hardness and dissolution test were performed in the same manner as that of Test Example 1. The results are shown in Table 4.

TABLE 4

|  | Example 9 | Example 10 |
|---|---|---|
| Hydrate of Compound A (mg) | 221.3 | 27.7 |
| Lactose hydrate (mg) | 13.9 | 31.1 |
| Carmellose calcium (mg) | 22.4 | 5.6 |
| Hydroxypropylcellulose (mg) | 8.4 | 2.1 |
| Light anhydrous silicic acid (mg) | 8.4 | 2.1 |
| Magnesium stearate (mg) | 5.6 | 1.4 |
| Opadry 03A48081 (mg) | 12.0 | 5.0 |
| Carnauba wax (mg) | Trace amount | Trace amount |
| Total (mg) | 292.0 | 75.0 |
| Dissolution ratio of Compound A (%) | 95.3 | 89.1 |
| Hardness of uncoated tablet (N) | 94 | 39 |

The film-coated tablet containing 221.3 mg of hydrate of Compound A (Example 9, the uncoated tablet had a diameter of 8.5 mm), and the film-coated tablet containing 27.7 mg of hydrate of Compound A (Example 10, the uncoated tablet had a diameter of 5.5 mm) showed superior dissolution property. Further, the uncoated tablets of Examples 9 and 10 had sufficient hardness in consideration of the diameters of the respective tablets.

TEST EXAMPLE 5

As a sample, the film-coated tablet of Example 11 was used.
Measurement of tablet hardness and dissolution test were performed in the same manner as that of Test Example 1. The results are shown in Table 5.

TABLE 5

|  | Example 11 |
|---|---|
| Hydrate of Compound A (mg) | 221.3 |
| Lactose hydrate (mg) | 13.9 |
| Carmellose calcium (mg) | 22.4 |
| Hydroxypropylcellulose (mg) | 8.4 |
| Hydrated silicon dioxide (mg) | 8.4 |
| Magnesium stearate (mg) | 5.6 |
| Opadry 03A48081 (mg) | 12.0 |
| Total (mg) | 292.0 |
| Dissolution ratio of Compound A (%) | 92.3 |
| Hardness of uncoated tablet (N) | 63 |

The film-coated tablet containing hydrated silicon dioxide (Example 11) showed superior dissolution property. Further, the uncoated tablet of Example 11 had sufficient hardness.

TEST EXAMPLE 6

As samples, the uncoated tablets of Example 13 and Comparative Example 3 were used.
Measurement of tablet hardness and dissolution test were performed in the same manner as that of Test Example 1. The results are shown in Table 6.

TABLE 6

|  | Example 13 | Comparative Example 3 |
|---|---|---|
| Hydrate of Compound A (mg) | 221.3 | 221.3 |
| Lactose hydrate (mg) | 22.3 | 30.7 |
| Low-substituted hydroxypropylcellulose (mg) | 14.0 | 14.0 |
| Hydroxypropylcellulose (mg) | 8.4 | 8.4 |

TABLE 6-continued

|  | Example 13 | Comparative Example 3 |
|---|---|---|
| Light anhydrous silicic acid (mg) | 8.4 | — |
| Magnesium stearate (mg) | 5.6 | 5.6 |
| Total (mg) | 280.0 | 280.0 |
| Light anhydrous silicic acid content (%) | 3 | 0 |
| Dissolution ratio of Compound A (%) | 82.3 | 61.0 |
| Hardness (N) | 127 | 112 |

The tablet containing 3% of light anhydrous silicic acid (Example 13) showed superior dissolution property compared with the tablet not containing light anhydrous silicic acid (Comparative Example 3).
Further, the tablet of Example 13 had sufficient hardness.
Hereafter, the present invention will be explained with reference to preparation examples, examples, and comparative examples. However, the present invention is not limited by these examples.
As the hydrate of Compound A, ¾hydrate of Compound A produced according to the method described in Preparation Example 1 was used.
As the coating agent, Opadry 03A48081 (hypromellose 2910:titanium oxide:talc=60:20:20, Colorcon Japan) was used, unless especially indicated.
The tablets of the examples and comparative examples had a circular shape (8.5 mm DR), unless especially indicated.

PREPARATION EXAMPLE 1

(1) Under a nitrogen atmosphere, 2-aminomalonamide (30 g, Tateyama Kasei) and oxalic acid (115 mg) were added to 2-propanol (600 mL), the mixture was heated to 82° C., and then triethyl orthoformate (106 mL, purity 99.5%, Nippoh Chemicals) was added dropwise to the mixture over 10 minutes. Then, the reaction mixture was stirred at 84° C. for 7 hours and 30 minutes. The reaction mixture was cooled to 57° C., and then water (30 mL) and concentrated hydrochloric acid (24 mL) were successively added to the reaction mixture. The reaction mixture was cooled to 5° C., and the crystals were collected by filtration, and washed with acetone (120 mL) to obtain 5-hydroxy-1H-imidazole-4-carboxamide hydrochloride dihydrate as pale yellow crystals (49 g).
(2) Under a nitrogen atmosphere, 5-hydroxy-1H-imidazole-4-carboxamide hydrochloride dihydrate (20.0 g) was added to 0.45 mol/L hydrochloric acid (240 mL), and dissolved therein by heating the mixture to 50° C. To this solution, a solution of sodium formate (14.3 g) dissolved in water (40 mL) was added dropwise over 33 minutes. The reaction mixture was cooled to 5° C., and the crystals were collected by filtration, washed with a mixture of acetone (20 mL) and water (40 mL), and then washed with acetone (60 mL) to obtain 5-hydroxy-1H-imidazole-4-carboxamide 3/4 hydrate as pale yellow crystals (12.8 g).

EXAMPLE 1

The hydrate of Compound A (4.5 g) and carmellose calcium (0.5 g, ECG-505, Nichirin Chemical Industries) were mixed in a mortar. To this mixed powder, a binder suspension {2.5 g, aqueous suspension of 8.7% hydroxypropylcellulose (HPC-L, Nippon Soda), 8.7% anhydrous citric acid (Komatsuya Corporation), and 4.3% light anhydrous silicic acid (Aerosil 200, Nippon Aerosil)} was added, and the mixture was granulated. The obtained granulated powder was dried at 40° C. for 2 hours, and passed through a sieve of 500-μm mesh, magnesium stearate (Merck) was added to the powder in an amount corresponding to 0.5% based on the tablet weight, and the mixture was kneaded and made into tablets by using a compression molding type tableting process analyzer (TAB FLEX, Okada Seiko) at a tableting pressure of 6 kN to obtain tablets having a weight of 300 mg per tablet.

EXAMPLE 2

The hydrate of Compound A (6 g), carmellose calcium (0.3 g, ECG-505, Nichirin Chemical Industries), lactose hydrate (0.3 g, Pharmatose 200M, DMV-Fonterra Excipients), and cornstarch (0.39 g, Nihon Shokuhin Kako) were mixed in a mortar. To this mixed powder, a binder suspension {3 g, aqueous suspension of 10% polyvinyl alcohol (Gohsenol EG-05, Japan Synthetic Chemical Industry), and 5% light anhydrous silicic acid (Aerosil 200, Nippon Aerosil)} was added, and the mixture was granulated. The obtained granulated powder was dried at 40° C. overnight, and then passed through a sieve of 500 μm mesh, magnesium stearate (Merck) was added to the powder in an amount corresponding to 0.8% based on the tablet weight, and the mixture was kneaded and made into tablets by using a compression molding type tableting process analyzer (TAB FLEX, Okada Seiko) at a tableting pressure of 6 kN to obtain tablets having a weight of 250 mg per tablet.

EXAMPLE 3

The hydrate of Compound A (6 g), carmellose calcium (0.3 g, ECG-505, Nichirin Chemical Industries), lactose hydrate (0.225 g, Pharmatose 200M, DMV-Fonterra Excipients), cornstarch (0.315 g, Nihon Shokuhin Kako), and anhydrous citric acid (0.15 g, Komatsuya Corporation) were mixed in a mortar. To this mixed powder, a binder suspension {3 g, aqueous suspension of 10% polyvinyl alcohol (Gohsenol EG-05, Japan Synthetic Chemical Industry), and 5% light anhydrous silicic acid (Aerosil 200, Nippon Aerosil)} was added, and the mixture was granulated. The obtained granulated powder was dried at 40° C. overnight, and then passed through a sieve of 500-μm mesh, magnesium stearate (Merck) was added to the powder in an amount corresponding to 0.8% based on the tablet weight, and the mixture was kneaded and made into tablets by using a compression molding type tableting process analyzer (TAB FLEX, Okada Seiko) at a tableting pressure of 6 kN to obtain tablets having a weight of 250 mg per tablet.

EXAMPLE 4

The hydrate of Compound A (9.957 g), carmellose calcium (0.585 g, ECG-505, Nichirin Chemical Industries), and lactose hydrate (0.398 g, Pharmatose 200M, DMV-Fonterra Excipients) were mixed by using a fluidized bed granulation dryer (minute quantity fluidized bed, Fuji Paudal). On this mixed powder, a binder suspension {7.02 g, aqueous suspension of 5% hydroxypropylcellulose (HPC-L, Nippon Soda), and 5% light anhydrous silicic acid (Aerosil 200, Nippon Aerosil)} was sprayed, and the powder was granulated and dried. To the obtained granulated powder, magnesium stearate (Merck) was added in an amount corresponding to 0.5% based on the tablet weight, and the mixture was kneaded and made into tablets by using a compression molding type tableting process analyzer (TAB FLEX, Okada Seiko) at a tableting pressure of 10 kN to obtain tablets having a weight of 260 mg per tablet.

EXAMPLE 5

The hydrate of Compound A (9.957 g), carmellose calcium (0.585 g, ECG-505, Nichirin Chemical Industries), and lactose hydrate (0.632 g, Pharmatose 200M, DMV-Fonterra Excipients) were mixed by using a fluidized bed granulation dryer (minute quantity fluidized bed, Fuji Paudal). On this mixed powder, a binder suspension {7.02 g, aqueous suspension of 5% hydroxypropylcellulose (HPC-L, Nippon Soda), and 1.5% light anhydrous silicic acid (Aerosil 200, Nippon Aerosil)} was sprayed, and the powder was granulated and dried. To the obtained granulated powder, magnesium stearate (Merck) was added in an amount corresponding to 0.5% based on the tablet weight, and the mixture was kneaded and made into tablets by using a compression molding type tableting process analyzer (TAB FLEX, Okada Seiko) at a tableting pressure of 10 kN to obtain tablets having a weight of 260 mg per tablet.

EXAMPLE 6

The hydrate of Compound A (9.957 g), carmellose calcium (0.585 g, ECG-505, Nichirin Chemical Industries), and lactose hydrate (0.714 g, Pharmatose 200M, DMV-Fonterra Excipients) were mixed by using a fluidized bed granulation dryer (minute quantity fluidized bed, Fuji Paudal). On this mixed powder, a binder suspension {7.02 g, aqueous suspension of 5% hydroxypropylcellulose (HPC-L, Nippon Soda), and 0.5% light anhydrous silicic acid (Aerosil 200, Nippon Aerosil)} was sprayed, and the powder was granulated and dried. To the obtained granulated powder, magnesium stearate (Merck) was added in an amount corresponding to 0.5% based on the tablet weight, and the mixture was kneaded and made into tablets by using a compression molding type tableting process analyzer (TAB FLEX, Okada Seiko) at a tableting pressure of 10 kN to obtain tablets having a weight of 260 mg per tablet.

EXAMPLE 7

The hydrate of Compound A (9.957 g), carmellose calcium (0.585 g, ECG-505, Nichirin Chemical Industries), and lactose hydrate (0.398 g, Pharmatose 200M, DMV-Fonterra Excipients) were mixed by using a fluidized bed granulation dryer (minute quantity fluidized bed, Fuji Paudal). On this mixed powder, a binder solution {7.02 g, aqueous solution of 5% hydroxypropylcellulose (HPC-L, Nippon Soda)} was sprayed, and the powder was granulated and dried. To the obtained granulated powder, light anhydrous silicic acid (Aerosil 200, Nippon Aerosil) and magnesium stearate (Merck) were added in amounts corresponding to 3% and 0.5% based on the tablet weight, respectively, and the mixture was kneaded and made into tablets by using a compression molding type tableting process analyzer (TAB FLEX, Okada Seiko) at a tableting pressure of 6 kN to obtain tablets having a weight of 260 mg per tablet.

EXAMPLE 8

The hydrate of Compound A (9.957 g), carmellose calcium (0.585 g, ECG-505, Nichirin Chemical Industries), lactose hydrate (0.398 g, Pharmatose 200M, DMV-Fonterra Excipients), and light anhydrous silicic acid (0.351 g, Aerosil 200, Nippon Aerosil) were mixed by using a fluidized bed granulation dryer (minute quantity fluidized bed, Fuji Paudal). On this mixed powder, a binder solution {7.02 g, aqueous solution of 5% hydroxypropylcellulose (HPC-L, Nippon Soda)} was sprayed, and the powder was granulated and dried. To the obtained granulated powder, magnesium stearate (Merck) was added in an amount corresponding to 0.5% based on the tablet weight, and the mixture was kneaded and made into tablets by using a compression molding type tableting process analyzer (TAB FLEX, Okada Seiko) at a tableting pressure of 6 kN to obtain tablets having a weight of 260 mg per tablet.

EXAMPLE 9

The hydrate of Compound A (442.52 g) ground by using a pin mill grinder (ALPINE Microgrinder 630, Powrex), carmellose calcium (44.8 g, ECG-505, Nichirin Chemical Industries), and lactose hydrate (27.88 g, Pharmatose 200M, DMV-Fonterra Excipients) were mixed by using a fluidized bed granulation dryer (FD-MP-01, Powrex). On this mixed powder, a binder suspension {336 g, aqueous suspension of 5% hydroxypropylcellulose (HPC-L, Nippon Soda), and 5% light anhydrous silicic acid (Aerosil 200, Nippon Aerosil)} was sprayed, and the powder was granulated and dried. To the obtained granulated powder, magnesium stearate (Merck) was added in an amount corresponding to 2% based on the uncoated tablet weight, and the mixture was kneaded and made into tablets by using a rotary tableting machine (HT-P18A, Hata Iron Works) at a tableting pressure of 10 kN to obtain tablets having a weight of 280 mg per tablet. The tablets were coated with the coating agent in an amount of 12 mg per uncoated tablet by using a coating machine (DRC-200, Powrex), and then subjected to a glazing treatment with carnauba wax (Polishing Wax 105, Nihon Wax) in an amount corresponding to 0.015% based on the uncoated tablet weight to obtain film-coated tablets.

EXAMPLE 10

The hydrate of Compound A (110.64 g) ground by using a pin mill grinder (ALPINE Microgrinder 630, Powrex), carmellose calcium (22.4 g, ECG-505, Nichirin Chemical Industries), and lactose hydrate (124.56 g, Pharmatose 200M, DMV-Fonterra Excipients) were mixed by using a fluidized bed granulation dryer (FD-MP-01, Powrex). On this mixed powder, a binder suspension {168 g, aqueous suspension of 5% hydroxypropylcellulose (HPC-L, Nippon Soda), and 5% light anhydrous silicic acid (Aerosil 200, Nippon Aerosil)} was sprayed, and the powder was granulated and dried. To the obtained granulated powder, magnesium stearate (Merck) was added in an amount corresponding to 2% based on the uncoated tablet weight, and the mixture was kneaded and made into tablets by using a rotary tableting machine (HT-P18A, Hata Iron Works) at a tableting pressure of 3 kN to obtain tablets of a circular shape (5.5 mm SR) having a weight of 70 mg per tablet. The tablets were coated with the coating agent in an amount of 5 mg per uncoated tablet by using a coating machine (DRC-200, Powrex), and then subjected to a glazing treatment with carnauba wax (Polishing Wax 105, Nihon Wax) in an amount corresponding to 0.015% based on the uncoated tablet weight to obtain film-coated tablets.

EXAMPLE 11

The hydrate of Compound A (221.26 g) ground by using a pin mill grinder (ALPINE Microgrinder 630, Powrex), carmellose calcium (22.4 g, ECG-505, Nichirin Chemical Industries), and lactose hydrate (13.94 g, Pharmatose 200M, DMV-Fonterra Excipients) were mixed by using a fluidized bed granulation dryer (FD-MP-01, Powrex). On this mixed powder, a binder suspension {168 g, aqueous suspension of 5% hydroxypropylcellulose (HPC-L, Nippon Soda), and 5% hydrated silicon dioxide (Carplex 80, Freund Corporation)} was sprayed, and the powder was granulated and dried. To the obtained granulated powder, magnesium stearate (Merck) was added in an amount corresponding to 2% based on the uncoated tablet weight, and the mixture was kneaded and made into tablets by using a rotary tableting machine (HT-P18A, Hata Iron Works) at a tableting pressure of 10 kN to obtain uncoated tablets having a weight of 280 mg per tablet. The tablets were coated with the coating agent in an amount of 12 mg per uncoated tablet by using a coating machine (DRC-200, Powrex) to obtain film-coated tablets.

EXAMPLE 12

The hydrate of Compound A (221.26 g) ground by using a pin mill grinder (ALPINE Microgrinder 630, Powrex) was mixed with lactose hydrate (13.94 g, Pharmatose 200M, DMV-Fonterra Excipients) and carmellose calcium (22.4 g, ECG-505, Nichirin Chemical Industries) by using a fluidized bed granulation dryer (FD-MP-01, Powrex). On this mixed powder, a binder suspension {168 g, aqueous suspension of 5% hydroxypropylcellulose (HPC-L, Nippon Soda), and 5% light anhydrous silicic acid (Aerosil 200, Nippon Aerosil)} was sprayed, and the powder was granulated and dried. To the obtained granulated powder, magnesium stearate (Merck) was added in an amount corresponding to 2% based on the uncoated tablet weight, and the mixture was kneaded and made into tablets by using a rotary tableting machine (HT-P18A, Hata Iron Works) at a tableting pressure of 10 kN to obtain tablets having a weight of 280 mg per tablet. The tablets were coated with a coating agent {Opadry 03A470001 TAN (60.00% of hypromellose 2910, 20.00% of talc, 18.86% of titanium oxide, 1.00% of yellow iron sesquioxide, 0.14% of black oxide of iron, Japan Colorcon)} in an amount of 10 mg per uncoated tablet by using a coating machine (DRC-200, Powrex), and then subjected to a glazing treatment with carnauba wax (Polishing Wax 105, Nihon Wax) in an amount corresponding to 0.015% based on the obtained tablet weight to obtain film-coated tablets. The composition of the film-coated tablets is shown in Table 7.

TABLE 7

|  | Example 12 Amount per tablet (mg) |
| --- | --- |
| Hydrate of Compound A | 221.3 |
| Lactose hydrate | 13.9 |
| Carmellose calcium | 22.4 |
| Hydroxypropylcellulose | 8.4 |
| Light anhydrous silicic acid | 8.4 |
| Magnesium stearate | 5.6 |
| Opadry 03A470001 | 10.0 |
| Carnauba wax | Trace amount |
| Total (mg) | 290.0 |

EXAMPLE 13

The hydrate of Compound A (11.06 g), low-substituted hydroxypropylcellulose (0.700 g, L-HPC LH-11, Shin-Etsu Chemical), and lactose hydrate (1.117 g, Pharmatose 200M, DMV-Fonterra Excipients) were mixed in a mortar. To this mixed powder, a binder suspension {5.444 g, aqueous suspension of 7.7% hydroxypropylcellulose (HPC-L, Nippon Soda), and 7.7% light anhydrous silicic acid (Aerosil 200, Nippon Aerosil)} was added, and the mixture was granulated. The obtained granulated powder was dried at 40° C. for 2 hours, and passed through a sieve of 500 μm mesh, magnesium stearate (Merck) was added to the powder in an amount corresponding to 2.0% based on the tablet weight, and the mixture was kneaded and made into tablets by using a rotary tableting machine (HT-P18A, Hata Iron Works) at a tableting pressure of 8 kN to obtain tablets having a weight of 280 mg per tablet.

COMPARATIVE EXAMPLE 1

According to the method described in Japanese Patent Publication (Kokoku) No. 1-37376, tablets were produced.

Specifically, the hydrate of Compound A (6 g), carmellose calcium (0.3 g, ECG-505, Nichirin Chemical Industries), lactose hydrate (0.375 g, Pharmatose 200M, DMV-Fonterra Excipients), and cornstarch (0.465 g, Nihon Shokuhin Kako) were mixed in a mortar. To this mixed powder, a binder solution {3 g, aqueous solution of 10% polyvinyl alcohol (Gohsenol EG-05, Japan Synthetic Chemical Industry)} was added, and the mixture was granulated. The obtained granulated powder was dried at 40° C. overnight, and then passed through a sieve of 500-μm mesh, magnesium stearate (Merck) was added to the powder in an amount corresponding to 0.8% based on the tablet weight, and the mixture was kneaded and made into tablets by using a compression molding type tableting process analyzer (TAB FLEX, Okada Seiko) at a tableting pressure of 6 kN to obtain tablets having a weight of 260 mg per tablet.

COMPARATIVE EXAMPLE 2

The hydrate of Compound A (9.957 g), carmellose calcium (0.585 g, ECG-505, Nichirin Chemical Industries), and lactose hydrate (0.749 g, Pharmatose 200M, DMV-Fonterra Excipients) were mixed by using a fluidized bed granulation dryer (minute quantity fluidized bed, Fuji Paudal). On this mixed powder, a binder solution {7.02 g, aqueous solution of 5% hydroxypropylcellulose (HPC-L, Nippon Soda)} was sprayed, and the powder was granulated and dried. To the obtained granulated powder, magnesium stearate (Merck) was added in an amount corresponding to 0.5% based on the tablet weight, and the mixture was kneaded and made into tablets by using a compression molding type tableting process analyzer (TAB FLEX, Okada Seiko) at a tableting pressure of 10 kN to obtain tablets having a weight of 260 mg per tablet.

COMPARATIVE EXAMPLE 3

The hydrate of Compound A (11.06 g), low-substituted hydroxypropylcellulose (0.700 g, L-HPC LH-11, Shin-Etsu Chemical), and lactose hydrate (1.537 g, Pharmatose 200M, DMV-Fonterra Excipients) were mixed in a mortar. To this mixed powder, a binder suspension {5.444 g, aqueous suspension of 7.7% hydroxypropylcellulose (HPC-L, Nippon Soda)} was added, and the mixture was granulated. The obtained granulated powder was dried at 40° C. for 2 hours, and passed through a sieve of 500-μm mesh, magnesium stearate (Merck) was added to the powder in an amount corresponding to 2.0% based on the tablet weight, and the mixture was kneaded and made into tablets by using a rotary tableting machine (HT-P18A, Hata Iron Works) at a tableting pressure of 8 kN to obtain tablets having a weight of 280 mg per tablet.

Industrial Applicability

The tablet of the present invention is useful as a tablet having a high content of Compound A or a salt thereof, or a hydrate thereof, and a tablet size that allows easy taking of the tablet, and showing superior dissolution property.

The invention claimed is:

1. A tablet containing (1) 5-hydroxy-1H-imidazole-4-carboxamide or a salt thereof, or a hydrate thereof, and (2) silicon dioxide, wherein silicon dioxide consists of one or more selected from light anhydrous silicic acid or hydrated silicon dioxide, wherein content of silicon dioxide is 0.1 to 20% of the mass of the tablet.

2. The tablet according to claim 1, which further contains an additive.

3. The tablet according to claim 2, wherein the additive consists of an additive containing a disintegrating agent.

4. The tablet according to claim 3, wherein the disintegrating agent consists of one or more selected from a cellulose derivative, a starch derivative, or a polyvinylpyrrolidone derivative.

5. The tablet according to claim 3, wherein the disintegrating agent consists of one or more selected from carmellose calcium, carmellose, low-substituted hydroxypropylcellulose, croscarmellose sodium, carboxymethyl starch sodium, partially pregelatinized starch, or crospovidone.

6. The tablet according to claim 3, wherein the disintegrating agent consists of one or more selected from carmellose calcium, low-substituted hydroxypropylcellulose, or partially pregelatinized starch.

7. The tablet according to claim 3, wherein the disintegrating agent is carmellose calcium.

8. The tablet according to claim 1, wherein content of 5-hydroxy-1H -imidazole-4-carboxamide or a salt thereof, or a hydrate thereof is 0.3 to 95% of the mass of the tablet.

9. The tablet according to claim 7, wherein content of 5-hydroxy-1H -imidazole-4-carboxamide or a salt thereof, or a hydrate thereof is 0.3 to 95% of the mass of the tablet.

10. A method for producing the tablet according to claim 1, wherein the tablet is made by using granulated powder produced by a wet granulation method.

11. The production method according to claim 10, wherein the wet granulation method is the fluidized bed granulation method.

* * * * *